United States Patent
Jeon et al.

(10) Patent No.: US 10,817,054 B2
(45) Date of Patent: Oct. 27, 2020

(54) EYE WATCH POINT TRACKING VIA BINOCULAR AND STEREO IMAGES

(71) Applicants: Samsung Electronics Co., Ltd., Suwon-si, Gyeonggi-do (KR); Korea University Research and Business Foundation, Seoul (KR)

(72) Inventors: Kang-won Jeon, Seoul (KR); Sung-Jea Ko, Seoul (KR); Tae-young Na, Hanam-si (KR); Mun-Cheon Kang, Pohang-si (KR); Sung-Ho Chae, Seoul (KR)

(73) Assignees: Samsung Electronics Co., Ltd., Suwon-si (KR); Korea University Research and Business Foundation, Seoul (KR)

( * ) Notice: Subject to any disclaimer, the term of this patent is extended or adjusted under 35 U.S.C. 154(b) by 131 days.

(21) Appl. No.: 16/122,382

(22) Filed: Sep. 5, 2018

(65) Prior Publication Data
US 2019/0073793 A1    Mar. 7, 2019

(30) Foreign Application Priority Data

Sep. 6, 2017  (KR) .................. 10-2017-0113647

(51) Int. Cl.
*G06F 3/01* (2006.01)
*G06K 9/00* (2006.01)
(Continued)

(52) U.S. Cl.
CPC .............. *G06F 3/013* (2013.01); *A61B 3/113* (2013.01); *G06K 9/00604* (2013.01); *G06T 7/74* (2017.01);
(Continued)

(58) Field of Classification Search
CPC ..... G06F 3/013; A61B 3/113; G06T 7/73–74; G06T 2207/10048; G06T 2207/10012;
(Continued)

(56) References Cited

U.S. PATENT DOCUMENTS

| 6,459,446 B1 | 10/2002 | Harman |
| 6,579,282 B2 | 6/2003 | Bille et al. |

(Continued)

FOREIGN PATENT DOCUMENTS

| EP | 0 634 031 B1 | 6/1999 |
| JP | 2007-94716 A | 4/2007 |

(Continued)

OTHER PUBLICATIONS

Acquisition of 3D Gaze Information from Eyeball Movements using Inside-out Camera (published in 2nd Augmented Human International Conference Jan. 2011).*

(Continued)

*Primary Examiner* — Casey L Kretzer
(74) *Attorney, Agent, or Firm* — Jefferson IP Law, LLP (57) ABSTRACT

An electronic apparatus is disclosed. The electronic apparatus includes an inputter configured to receive a binocular image which is a captured image of both eyes of a user and a stereo image which is an image of a direction corresponding to a gaze of the user captured at locations spaced apart from each other, and a processor configured to detect a watch point of a user in the stereo image by using the binocular image, obtain a disparity map in the input stereo image, and compensate the detected watch point using the obtained disparity map.

15 Claims, 8 Drawing Sheets

(51) Int. Cl.

| | | |
|---|---|---|
| *H04N 13/239* | (2018.01) | |
| *G06T 7/73* | (2017.01) | |
| *A61B 3/113* | (2006.01) | |
| *H04N 13/204* | (2018.01) | |
| *H04N 13/00* | (2018.01) | |

(52) U.S. Cl.
CPC . *H04N 13/239* (2018.05); *G06T 2207/10012* (2013.01); *G06T 2207/10048* (2013.01); *G06T 2207/30201* (2013.01); *H04N 13/204* (2018.05); *H04N 2013/0081* (2013.01)

(58) Field of Classification Search
CPC ........ G06T 2207/30201; H04N 13/239; H04N 13/204; H04N 2013/0081; G06K 9/00604
See application file for complete search history.

(56) References Cited

U.S. PATENT DOCUMENTS

| | | | |
|---|---|---|---|
| 7,857,452 | B2 | 12/2010 | Martinez-Conde et al. |
| 9,361,519 | B2 | 6/2016 | Horesh et al. |
| 2007/0069872 | A1 | 3/2007 | Arakawa et al. |
| 2011/0234765 | A1 | 9/2011 | Tanaka |
| 2012/0314933 | A1 | 12/2012 | Morifuji et al. |
| 2013/0120712 | A1 | 5/2013 | Spasovski |
| 2015/0286070 | A1 | 10/2015 | Aikawa |
| 2016/0042240 | A1* | 2/2016 | Takeda ............. A61B 5/18 382/104 |
| 2016/0150210 | A1* | 5/2016 | Chang ............. G06T 7/593 382/154 |
| 2016/0249800 | A1 | 9/2016 | Horesh et al. |
| 2019/0033058 | A1* | 1/2019 | Tsurumi .......... G06T 19/00 |

FOREIGN PATENT DOCUMENTS

| | | | | |
|---|---|---|---|---|
| JP | 2011-203811 | A | 10/2011 | |
| JP | 2012-257022 | A | 12/2012 | |
| JP | 2017-37329 | A | 2/2017 | |
| KR | 10-2015-0080372 | A | 7/2015 | |
| WO | WO-2017134886 | A1 * | 8/2017 | ............. G01B 11/02 |

OTHER PUBLICATIONS

Beymer et al, Eye Gaze Tracking Using An Active Stereo Head (published in 2003 IEEE Computer Society Conference on Computer Vision and Pattern Recognition Jun. 2003.*
Pirri et al., "A General Method for the Point of Regard Estimation in 3D Space," Dipartimento di Informatica e Sistemistica Sapienza Universit'a di Roma via Ariosto 25, 00185 Rome, Italy 2011.
Hennessey et al., "Noncontact Binocular Eye-Gaze Tracking for Point-of-Gaze Estimation in Three Dimensions," IEEE Trans. Biomedical engineering, Mar. 2009.
Wibirama et al., "3D Gaze Tracking System for NVidia 3D Vision," IEEE Conf. Engineering in Medicine and Biology Society (EMBC), p. 3194-3197, Osaka, Japan, Jul. 3-7, 2013.
Kwon et al., "Selective attentional point-tracking through a head-mounted stereo gaze tracker based on trinocular epipolar geometry," I2MTC, 2015.
Qodseya et al., "A3D: A Device for Studying Gaze in 3D," Springer International Publishing Switzerland; pp. 572-588; 2016.
Helmut Schrom-Feiertag et al., "Evaluation of indoor guidance systems using eye tracking in an immersive virtual environment," Spatial Cognition & Computation An Interdisciplinary Journal; pp. 163-183; 2017.
Marketsandmarkets.com, "Head-Up Display Market by Component (Video Generator, Projector/Projection Unit, Display Unit, Software), Type (Conventional HUD, AR-Based HUD), Application (Aviation, Automotive), and Geography—Global Forecast to 2023," https://www.marketsandmarkets.com/Market-Reports/head-up-display-hud-market-684.html.
Ma et al., An Invitation to 3-D Vision: From Images to Models, Springer, Nov. 19, 2001; pp. 44-59.
Hartley et al., "Triangulation," Computer vision and image understanding 68.2 (1997): 146-157.
Hartley et al., "Multiple View Geometry in computer vision," Cambridge university press, 2003.
Stephen Peterson and Ella Pinska, "Human Performance with simulated Collimation in Transparent Projection Screens." Proc. 2nd Int. Conf. Research in Air Transportation, pp. 231-237, 2006.
James E. Cutting, "How the eye measures reality and virtual reality," Behavior Research Methods, Instruments, & Comput., vol. 29, No. 1, pp. 27-36, Mar. 1997.
Santner et al., "Visual Recovery of Saliency Maps from Human Attention in 3D Environments," Joanneum Research Forschungsgesellschaft mbH, Graz, Austria, 2013.
T. Kowsari et al., "Multi-Depth Cross-Calibration of Remote Eye Gaze Trackers and Stereoscopic Scene Systems," IEEE Intelligent Vehicles Symposium, 2014.
Pieszala et al., "3D Gaze Point Localization and Visualization Using LiDAR-based 3D Reconstructions," 2016.
Bellini et al., "Profiles in Innovation Virtual & Augmented"; The Goldman Sachs Group, Inc; http://www.goldmansachs.com/our-thinking/pages/technology-driving-innovation-folder/virtual-and-augmented-reality/report.pdf.
Cartelligent, "Should your next car have Head-Up Display?"; http://www.cartelligent.com/blog/should-your-next-car-have-head-display, 2018.
Hudway, "Hudway Go—The app for less-distracting navigation. Made for drivers by drivers"; http://hudwayapp.com, 2018.
S. Bernet et al. "Study on the interest of hybrid fundamental matrix for head mounted eye tracker modeling." BMVC. 2011.
S. Bernet et al., "Autocalibration-based partioning relationship and parallax relation for head-mounted eye trackers." Machine vision and applications vol. 24, No. 2, pp. 393-406, 2013.
K. Yamaguchi et al., "Efficient Joint Segmentation, Occlusion Labeling, Stereo and Flow Estimation," 13th European Conf. Computer Vision, Zurich, Switzerland, 2014, pp. 756-771.
N. Einecke and J. Eggert, "A Two-Stage Correlation Method for Stereoscopic Depth Estimation," Int. Conf. Digital Image Computing: Techniques and Applications, Sydney, Australia, 2010, pp. 227-234.
H. Hirschmueller, "Stereo Processing by Semi-Global Matching and Mutual Information," IEEE Trans. Pattern Anal. Mach. Intell., vol. 30, No. 2, pp. 328-341, Dec. 2007.
A. Geiger, M. Roser, and R. Urtasun, "Efficient Large-Scale Stereo Matching," 10th Asian Conf. Computer Vision, Queenstown, New Zealand, 2010, pp. 25-38.
G. Bradski. (Nov. 1, 2000). The OpenCV Library. [Online]. Available: http:// http://www.drdobbs.com/open-source/the-opencv-library/184404319.

* cited by examiner

EYE WATCH POINT TRACKING VIA BINOCULAR AND STEREO IMAGES

CROSS-REFERENCE TO RELATED APPLICATIONS

This application claims priority from Korean Patent Application No. 10-2017-0113647, filed on Sep. 6, 2017 in the Korean Intellectual Property Office, the disclosure of which is incorporated herein by reference in its entirety.

BACKGROUND

Field

Aspects of the embodiments relate to an electronic apparatus, a controlling method thereof, and a computer readable recording medium, and more particularly, to an electronic apparatus for detecting a watch point of a user in a three-dimensional space, a controlling method thereof, and a computer readable recording medium.

Description of the Related Art

The trend of smartphones and tablet PCs that have swept the world for several years has changed from consumption tendency to lifestyle patterns. That much, IT apparatuses are in close relationship with our daily lives these days. This is because of that new technologies which could be seen in a movie before can be easily used by anyone now. One of the representative new technologies is an 'Augmented Reality (AR)'.

Detecting an object gazed by a user in a three-dimensional space from the user's gaze is a basic interface for Human-computer interaction (HCI) in the system such as a Head-up display (HUD) and the like.

The technology for tracking a user's gaze in a three-dimensional space has been actively studied as an important element technology for an object recognition and the HCI. Tracking the user's gaze in a three-dimensional space has been basically performed based on the observation of user's eyes and the result thereof. However, only with the binocular observation result, there is a limitation in accurately finding the watch point in three-dimensional space at a distance as a limitation of a measurement accuracy.

Thus, recently, in order to improve the tracking performance and to utilize the results thereof for an object recognition, a computer interaction, etc., a method of additionally using a camera for capturing the same gaze direction as the user has been actively studied. Specifically, it is necessary to perform a precise matching process between the binocular gaze vector which is derived by observing both eyes and the image of the user's gaze direction. Even if a precise matching is performed in advance, there is a problem that it is difficult to accurately detect the watch point in a three-dimensional space because of a binocular visual vector error, a match error, etc.

Accordingly, in order to accurately detect the watch point in a three-dimensional space of a user, a need for the technology for compensating the error in gaze vector has been raised.

SUMMARY

An aspect of the embodiment has been made to address the problems described above and to provide an electronic apparatus for accurately detecting a watch point of a user in a three-dimensional space using a disparity map, a controlling method thereof, and a computer readable recording medium.

According to an embodiment, there is provided an electronic apparatus including an inputter configured to receive a binocular image which is a captured image of both eyes of a user and a stereo image which is an image of a direction corresponding to a gaze of the user captured at locations spaced apart from each other, and a processor configured to detect a watch point of a user in the stereo image by using the binocular image, obtain a disparity map in the input stereo image, and compensate the detected watch point using the obtained disparity map.

In this case, the stereo image may include a first image corresponding to a left eye of a user and a second image corresponding to a right eye of a user, and the processor may detect a left eye watch point of a user in the first image and a right eye watch point in the second image by using the binocular image, obtain a first disparity map and a second disparity map by performing stereo matching of the first image and the second image, and compensate the detected left eye watch point and the detected right eye watch point by using the first disparity map and the second disparity map.

In this case, the processor may compensate the detected left eye watch point and the detected right eye watch point using the first disparity map and the second disparity map to minimize a difference between a disparity of the left eye watch point and a disparity of the right eye watch point.

The processor may compensate the detected left eye watch point and the detected right eye watch point to minimize a difference between a location of the left eye watch point and a location of the right eye watch point in a state in which horizontal deviation of the first image and the second image is compensated.

The processor may compensate vertical deviation of the first image and the second image, and perform stereo matching using the compensated first image and the compensated second image.

The processor may obtain a three dimensional watch point using the compensated left eye watch point and the compensated right eye watch point.

The processor may obtain vector and distance information of a binocular gaze using the compensated left eye watch point and the compensated right eye watch point.

The inputter may include an infrared camera configured to captures both eyes of the user, and a stereo camera configured to captures a direction corresponding to a gaze of the user at locations spaced apart from each other.

According to an embodiment, there is provided a method for controlling an electronic apparatus including receiving a binocular image which is a captured image of both eyes of a user and a stereo image which is an image of a direction corresponding to a gaze of the user captured at locations spaced apart from each other, detecting a watch point of a user in the stereo image by using the binocular image, obtaining a disparity map in the input stereo image, and compensating the detected watch point using the obtained disparity map.

In this case, the stereo image may include a first image corresponding to a left eye of a user and a second image corresponding to a right eye of a user, the detecting the watch point may include detecting a left eye watch point of a user in the first image and a right eye watch point in the second image by using the binocular image, the obtaining may include obtaining a first disparity map and a second disparity map by performing stereo matching of the first image and the second image, and the compensating may include compensating the detected left eye watch point and the detected right eye watch point by using the first disparity map and the second disparity map.

The compensating may include compensating the detected left eye watch point and the detected right eye watch point using the first disparity map and the second disparity map to minimize a difference between a disparity of the left eye watch point and a disparity of the right eye watch point.

The compensating may include compensating the detected left eye watch point and the detected right eye watch point to minimize a difference between a location of the left eye watch point and a location of the right eye watch point in a state in which horizontal deviation of the first image and the second image is compensated.

The controlling method may further include compensating vertical deviation of the first image and the second image, and the obtaining may include performing stereo matching using the compensated first image and the compensated second image.

The controlling method may further include obtaining a three dimensional watch point using the compensated left eye watch point and the compensated right eye watch point.

The controlling method may further include obtaining vector and distance information of a binocular gaze using the compensated left eye watch point and the compensated right eye watch point.

The receiving may include capturing both eyes of the user using an infrared camera, and capturing a direction corresponding to a gaze of the user at locations spaced apart from each other.

According to an embodiment, there is provided a computer readable recording medium which includes a program to execute a method for controlling an electronic apparatus including receiving a binocular image which is a captured image of both eyes of a user and a stereo image which is an image of a direction corresponding to a gaze of the user captured at locations spaced apart from each other, detecting a watch point of a user in the stereo image by using the binocular image, obtaining a disparity map in the input stereo image, and compensating the detected watch point using the obtained disparity map.

DETAILED DESCRIPTION

Terms used in the present disclosure will be briefly explained, and embodiments will be described in great detail.

Terms used in the present disclosure are selected as general terminologies currently widely used in consideration of the configuration and functions of the present disclosure, but can be different depending on intention of those skilled in the art, a precedent, appearance of new technologies, and the like. Further, in specific cases, terms may be arbitrarily selected. In this case, the meaning of the terms will be described in the description of the corresponding embodiments. Accordingly, the terms used in the description should not necessarily be construed as simple names of the terms, but be defined based on meanings of the terms and overall contents of the present disclosure.

The embodiments may vary, and may be provided in different example embodiments. Various embodiments will be described with reference to accompanying drawings. However, this is not intended to limit the scope to an embodiment, and therefore, it should be understood that all the modifications, equivalents or substitutes included under the invented spirit and technical scope are encompassed. In describing the embodiments, well-known functions or constructions are not described in detail since they would obscure the specification with unnecessary detail.

The terms such as "first," "second," and so on may be used to describe a variety of elements, but the elements should not be limited by these terms. The terms are used simply to distinguish one element from other elements.

Singular forms are intended to include plural forms unless the context clearly indicates otherwise. In the embodiments, the terms "include" and "comprise" designate the presence of features, numbers, steps, operations, components, elements, or a combination thereof that are written in the specification, but do not exclude the presence or possibility of addition of one or more other features, numbers, steps, operations, components, elements, or a combination thereof.

In an embodiment, 'a module' or 'a unit' performs at least one function or operation, and may be realized as hardware, software, or combination thereof. In addition, a plurality of 'modules' or 'units' may be integrated into at least one module and may be realized as at least one processor in an integrated manner except for 'modules' or 'units' that should be realized in specific hardware.

Hereinafter certain embodiments will now be described in greater detail with reference to the accompanying drawings to enable those skilled in the art to work the same with ease. However, embodiments may be realized in a variety of different configurations, and not limited to descriptions provided herein. Further, those that are irrelevant with the description are omitted so as to describe exemplary embodiments more clearly, and similar drawing reference numerals are used for the similar elements throughout the description.

Below, embodiments will be described in detail with reference to the attached drawings.

Figure 1:
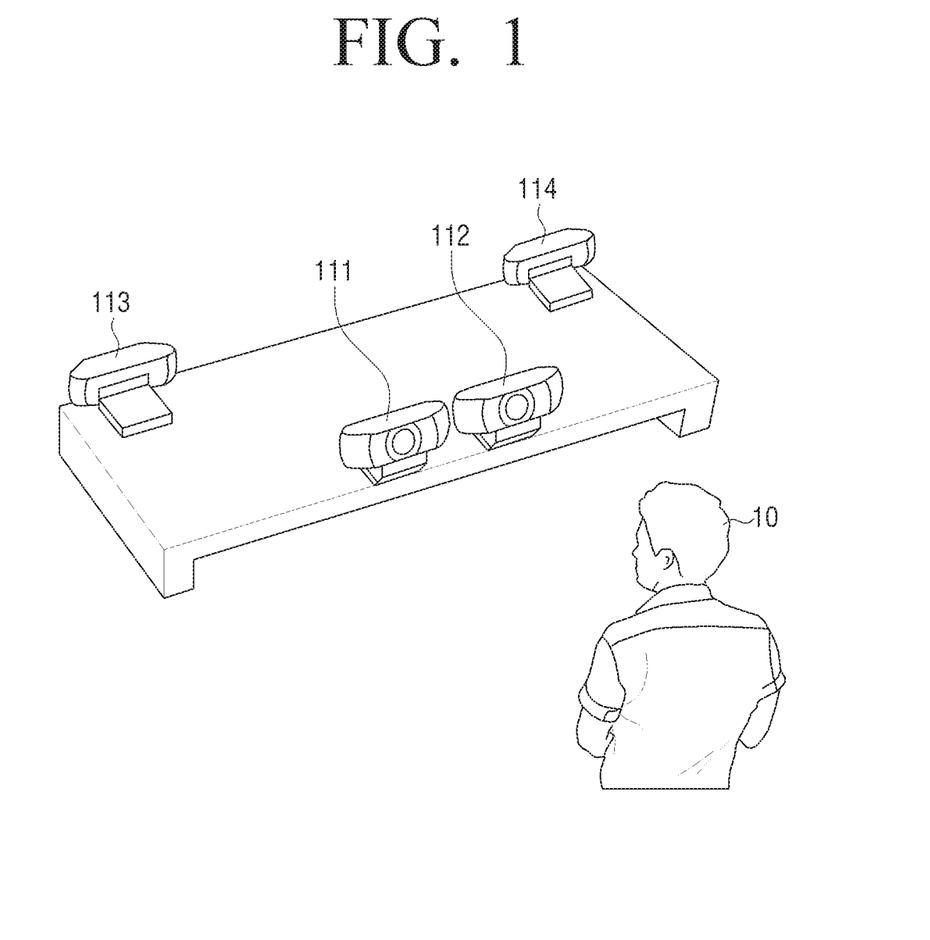
FIG. 1 is a view illustrating a system for detecting a watch point of a user in a three-dimensional space according to an embodiment.

FIG. 1 is a view illustrating a system for detecting a watch point of a user in a three-dimensional space according to an embodiment.

Referring to FIG. 1, the system to detect a watch point of a user 10 according to an embodiment may include a plurality of cameras 111 and 112 that capture both eyes of the user 10 and a plurality of cameras 113 and 114 that capture a direction to which the user 10 is watching.

Specifically, the plurality of cameras 111 and 112 that capture both eyes of the user 10 may include the camera 111 that captures a left eye of the user 10 and the camera 112 that captures a right eye of the user 10. Here, the plurality of cameras 111 and 112 that capture both eyes of the user 10 may be for detecting the gaze of the user 10. Here, the plurality of cameras 111 and 112 that capture both eyes of the user 10 may be an infrared camera or a general camera using visible light.

Meanwhile, FIG. 1 illustrates that the plurality of cameras capture both eyes of the user 10 respectively, but in the implementation, one camera may capture both eyes of a user and in the image of the both eyes, a left eye and a right eye of the user 10 may be detected respectively.

Meanwhile, the plurality of cameras 113 and 114 that capture a direction where the user 10 is watching may include the camera 113 that captures the direction where a left eye of the user is watching and the camera 114 that captures the direction where a right eye of the user 10 is watching. Here, the plurality of cameras 113 and 114 that capture the direction where the user 10 is watching is for capturing an image of the area where the user 10 is presumed to be watching. Here, the plurality of cameras 113 and 114 that capture the direction where the user is watching may be stereo cameras to obtain a stereoscopic image.

Meanwhile, in the system to detect a watch point of a user in a three-dimensional space, the watch point of a user in a stereo image may be detected using a binocular image of the user 10 captured by the plurality of cameras 111 and 112 that capture the both eyes of the user 10 and using a stereo image captured by the plurality of cameras 113 and 114 that capture the direction being gazed by the user 10, and the detected watch point may be compensated using a disparity map obtained with the stereo image. Meanwhile, a method for compensating the detected watch point will be described in detail with reference to FIGS. 2 to 8 below.

Figure 2:
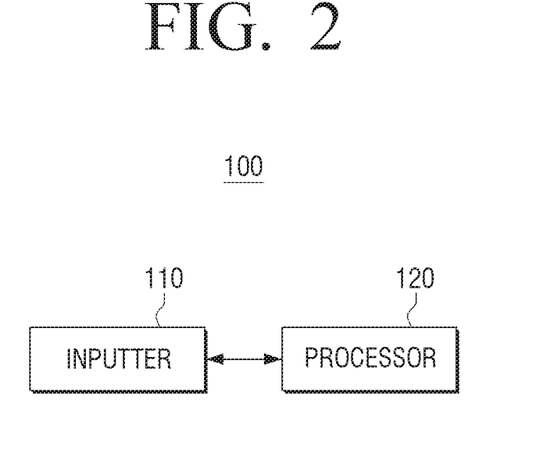
FIG. 2 is a block diagram illustrating a brief configuration of an electronic apparatus according to an embodiment.

FIG. 2 is a block diagram illustrating a brief configuration of an electronic apparatus according to an embodiment.

Referring to FIG. 2, the electronic apparatus 100 may include an inputter 110 and a processor 120.

The inputter 110 may receive a binocular image which is an image of both eyes of a user. Here, the inputter 110 may receive a plurality of images in which both eyes of the user are captured respectively, or receive one image in which both eyes of the user are captured at the same time.

Specifically, the inputter 110 may include at least one camera to capture both eyes of a user. Here, the inputter 110 may include at least one camera when capturing both eyes of the user at the same time, and when capturing both eyes respectively, the inputter 110 may include at least two or more than two cameras. Here, the inputter 110 may capture both eyes of the user with an infrared camera or a general camera using visible light.

In addition, the inputter 110 may receive a stereo image which is an image of the direction corresponding to the gaze of the user, captured at locations spaced apart from each other.

Specifically, the inputter 110 may include a camera for capturing a direction corresponding to the gaze of a left eye of a user and a camera for capturing a direction corresponding to the gaze of a right eye of the user. Here, a plurality of images in which each direction corresponding to the user's gaze is captured respectively may be called a stereo image. Here, the stereo image may include a left eye image corresponding to a left eye of a user and a right eye image corresponding to a right eye of a user. In addition, practically there is a difference between the area where the left eye gazes and the area where the right eye gazes because of the distance between the left eye and the right eye of the user, and thus the first image and the second image may be generated so that there is a difference in the locations of the corresponding points in each image.

Meanwhile, if a camera is not included in the electronic apparatus 100, the inputter 110 may include a communicator (not illustrated) that receives a binocular image and a stereo image from an external camera.

The processor 120 may detect a watch point of a user in a stereo image using the binocular image received by the inputter 110. Specifically, the processor 120 may detect a left eye watch point watched by the left eye in the left eye image corresponding to the left eye by using a gaze vector of the left eye detected in the received binocular image. In addition, the processor 120 may detect a right eye watch point watched by the right eye in the right eye image corresponding to the right eye using a gaze vector of the right eye detected in the received binocular image.

In addition, the processor 120 may generate a disparity map using a stereo image. Specifically, the processor 120 may generate the disparity map regarding each of the left eye image and the right eye image. Specifically, the processor 120 may perform stereo matching of the left eye image and the right eye image and generate the disparity map regarding each image. Here, the stereo matching may mean that distance information is extracted using the degree of difference between the corresponding points in two images in different watch point.

This reflects that there is a difference in the areas watched by a left eye and a right eye according to the distance between the left eye and the right eye, and the map is generated by using that if the same object is near in an image, there is a big difference between the locations of the object in two images, and if the distance between the same object is far, there is a small difference between the locations of the object in two images. As such, the distance information between the location of the object and the location in which a camera is located in the image may be known by using the disparity map.

Here, the processor 120 may compensate the vertical deviation of the left eye image and the right eye image which are input stereo images. According thereto, there is only a left-right deviation in the location of the corresponding points in the left eye image and the right eye image in which the vertical deviation is compensated, further accurate detection of a watch point become possible. In addition, the processor 120 performs stereo matching of the compensated left eye image and right eye image and generates the disparity map regarding each of the left eye image and the right eye image.

The processor 120 may compensate the detected watch point using the generated disparity map. Specifically, the processor 120 may compensate the location of the left eye watch point and the location of the right eye watch point using the disparity map generated regarding the left eye image and the disparity map generated regarding the right eye image.

Specifically, the processor 120 may calculate the range in which the compensation may be performed regarding each watch point based on the detected left eye watch point and right eye watch point, and compensate the left eye watch point and right eye watch point within the calculated range.

Specifically, the processor 120 may compensate the location of the detected left eye watch point and the location of the right eye watch point so that the difference between the location of the left eye watch point and the location of the right eye watch point to be minimized. Specifically, in the state in which a horizontal deviation of the left eye image and right eye image is compensated, the processor 120 may compensate the locations of the detected left eye watch point and detected right eye watch point so that the difference between the locations of the left eye watch point in the left eye image in which the horizontal deviation is compensated and the location of the right eye watch point in the right eye image in which the horizontal deviation is compensated, is minimized. Meanwhile, in the state in which the horizontal deviation of the left eye image and right eye image is not compensated, the processor 120 may compensate the location of the detected left eye watch point and the location of the detected right eye watch point to be converged to the difference in the locations of the corresponding points in the left eye image and the right eye image.

In addition, the processor 120 may compensate the locations of the detected left watch point and the detected right watch point by using the disparity map generated regarding the left eye image and the disparity map generated regarding the right eye image so the difference in the disparity of the left watch point and the right watch point to be minimized. This is because of that even if the difference of distance is not big in a two-dimensional image, if watch point is detected on different areas respectively based on the boundary of an object, it is difficult to determine the watch point as a watch point that a user is watching.

Meanwhile, the processor 120 may select an optimum compensated left eye watch point ($\hat{X}'_1$) and an optimum compensated right eye watch point ($\hat{X}'_2$) that satisfy the following formula (1) in which the above described compensation method is reflected within the calculated compensable area.

$$\operatorname{argmin}[\{d(x'_1, \hat{x}'_1)^2 + (x'_2, \hat{x}'_2)^2\} + \lambda\{(M_1(\hat{x}'_1) - M_2(\hat{x}'_2))^2 + (M_1(\hat{x}'_1) - d(\hat{x}'_1, \hat{x}'_2))^2 + (M_2(\hat{x}'_2) - d(\hat{x}'_1, \hat{x}'_2))^2\}] \quad (1)$$

Here, x1' and x2' may mean the locations of the left eye watch point and the right eye watch point detected from each stereo image in which vertical deviation is compensated, M1(x) and M2(x) may mean disparity values in a specific location from each stereo image in which vertical deviation is compensated, and d($\hat{X}'_1$, $\hat{X}'_2$), may mean a relative coordinate difference between the compensated left eye watch point ($\hat{X}'_1$) and the compensated right eye watch point ($\hat{X}'_2$) in the stereo image in which a vertical deviation is compensated.

Referring to formula (1), the processor 120 may select $\hat{X}'_1$ and $\hat{X}'_2$ so that a location change of the detected watch point and the compensated watch point is minimum, and the disparity difference of the watch point in each disparity map is minimum.

In addition, the processor 120 may select $\hat{X}'_1$ and $\hat{X}'_2$ so that each of the disparity of the compensated left eye watch point and the disparity of the compensated right eye watch point, and a relative coordinate difference between the compensated left eye watch point ($\hat{X}'_1$) and the compensated right eye watch point ($\hat{X}'_2$) to be minimum. This is because of that the disparity of the watch point is calculated by the difference between each corresponding point in the stereo image.

In addition, the processor 120 may generate a three-dimensional watch point using the compensated left eye watch point and the compensated right eye watch point. Specifically, since the left eye watch point and the right eye watch point primarily detected in the stereo image are not matched, a three-dimensional watch point could not be generated or generated in an inaccurate location, but by using the compensated left eye watch point and the compensated right eye watch point, further accurate three-dimensional watch point may be generated.

In addition, the processor 120 may generate a vector and distance information of a binocular gaze using the compensated left eye watch point and the compensated right eye watch point. Specifically, the processor 120 may generate the vector and distance information of the binocular gaze regarding the generated three-dimensional watch point.

As described above, according to compensating the left eye watch point and the right eye watch point using the disparity map, further accurate watch point of a user in a three-dimensional space may be detected.

Figure 3:
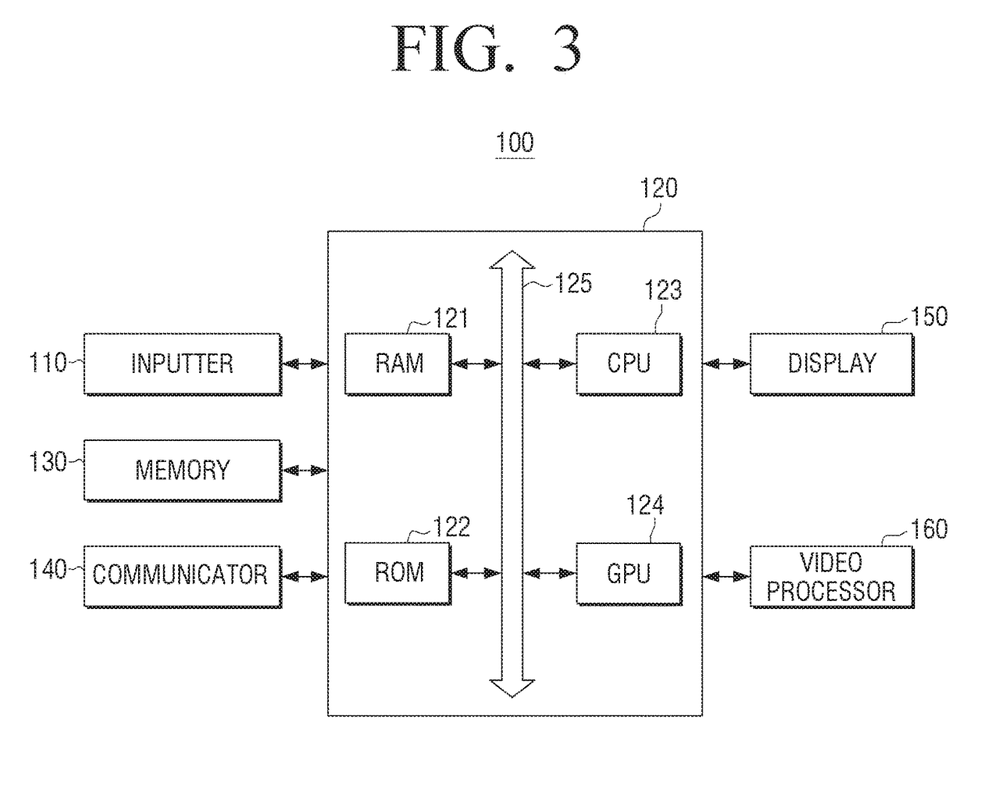
FIG. 3 is a block diagram illustrating a specific configuration of an electronic apparatus of FIG. 2.

FIG. 3 is a block diagram illustrating a specific configuration of an electronic apparatus of FIG. 2.

Referring to FIG. 3, the electronic apparatus 100 may include the inputter 110, the processor 120, the memory 130, the communicator 140, the display 150 and a video processor 160. Here, some operations of the inputter 110 and the processor 120 are the same as the configuration described in FIG. 2, and thus overlapping descriptions will be omitted.

The processor 120 may include a random access memory (RAM) 121, a read only memory (ROM) 122, a central processing unit (CPU) 123, a graphic processing unit (GPU) 124, and a bus 125. The RAM 121, the ROM 122, the CPU 123, the GPU 124, and so on may be connected to each other through the bus 125.

The CPU 123 accesses the memory 140 to perform booting using the O/S stored in the memory 140. The CPU 123 may perform various operations by using the various programs, contents, data, and the like stored in the memory 140.

The ROM 122 stores a set of instructions for system booting. When a turn-on command is input and thus the power is supplied, the CPU 123 may copy the O/S stored in the memory 180 to RAM 121 according to the instructions stored in the ROM 122, and boot the system by executing the O/S. When the booting is completed, the CPU 123 may copy the various programs stored in the memory 140 to the RAM 121, and perform various operations by implementing the programs copied to the RAM 121.

The GPU 124 may display a UI on the display 170 when the booting of the electronic apparatus 100 is completed. In detail, the GPU 124 may generate a screen including various objects such as an icon, an image, a text, etc. using a calculator (not shown) and a renderer (not shown). The calculator may calculate attribute values such as coordinates, shape, size, and color of each object to be displayed according to the layout of the screen. The renderer may generate screens of various layouts including objects based on the attribute value calculated in the operation unit. The screens (or user interface window) generated in the renderer may be provided to the display, and displayed on each of a main display area and a sub display area. Meanwhile, it has been described that the image processing operation according to an embodiment is performed by the GPU 124, but in the implementation, the operation may be performed by the CPU 123 or the GPU 124.

The memory 130 may be realized as a recording medium in the electronic apparatus 100 or as an external storage medium, such as a removable disk including a USB memory, a web server via network, and the like. Specifically, the memory 130 may include a hard disk, SSD, a memory card, a ROM, a USB memory and the like.

Specifically, the memory 130 may store the information on the binocular watch point detected by using the binocular image and a stereo image input through the inputter 110. In addition, the memory 130 may store the disparity map separately generated with regard to the stereo image. In addition, the memory 130 may store the information regarding the compensated binocular watch point using the disparity map by the processor 120.

In addition, the memory 130 may store the information on the three-dimensional watch point generated by using the compensated binocular watch point. Specifically, the information on the three-dimensional watch point may include location information and distance information in the stereo image. Here, the location information in the stereo image may include the information on a binocular gaze vector.

The communicator 140 may communicate with various types of external apparatus according to various types of communication method. Specifically, the communicator 140 may communicate with an external apparatus such as a capturing apparatus, an external server, an external display apparatus and the like.

Specifically, the communicator 140 may receive a plurality of images from an external apparatus through a wired method such as an antenna, a cable, or a port, or receive a plurality of images through a wireless method such as Wi-Fi and Bluetooth.

In addition, the communicator 140 may transmit the information on the binocular watch point compensated by an operation of the processor 120 and the information on a three-dimensional watch point generated by the compensated binocular watch point, to an external apparatus.

Meanwhile, FIG. 3 illustrates that the inputter 110 and the communicator 140 are an additional configuration, but the electronic apparatus 100 may not include a capturing unit or the inputter 110 may include some or all functions of the communicator 140 by a setting.

The display 150 may display the image corresponding to the generated three-dimensional watch point. Specifically, the display 150 may further display a curser and the like at the location corresponding to the three-dimensional watch point being watched by a user in the stereoscopic image generated by using a stereo image.

The video processor 160 is an element for processing the content received through the communicator 140 or video data included in the content stored in the memory 130 when the display 150 is included in the electronic apparatus 100. The video processor 160 may perform various image processing processes such as decoding, scaling, noise filtering, frame rate conversion, resolution conversion, conversion into a stereoscopic image using the stereo image on video data.

In addition, the video processor 160 may process image processing on the video data based on the user's gaze detected by the processor 120. Specifically, the video processor 160 may process image processing to display a cursor and the like on the received stereoscopic image based on the three-dimensional watch point generated by the compensated binocular watch point.

Figure 4:
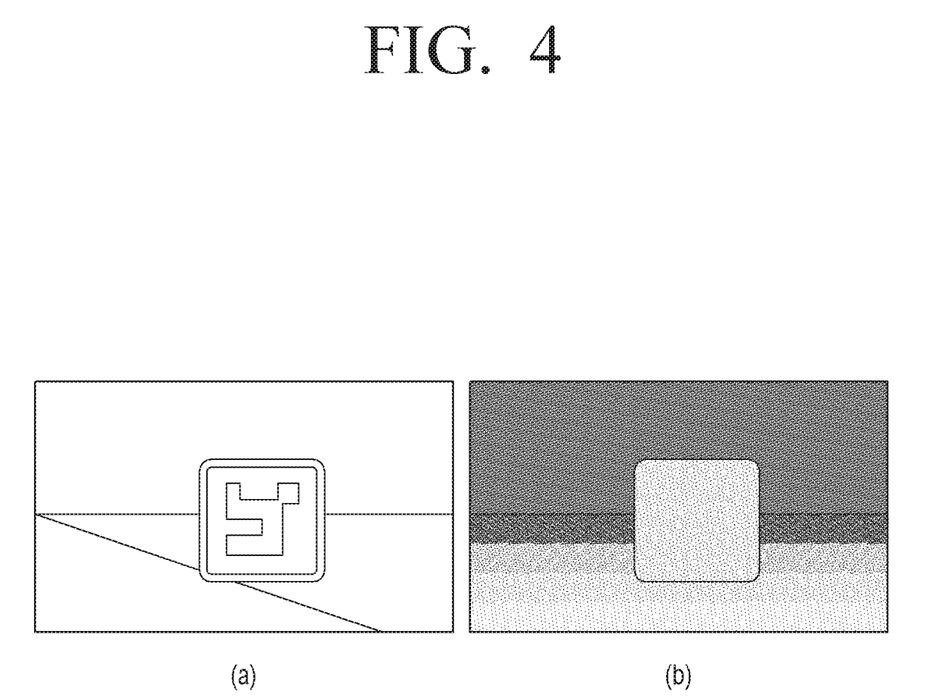
FIG. 4 is a view illustrating a disparity map according to an embodiment.

FIG. 4 is a view illustrating a disparity map according to an embodiment. Specifically, an electronic apparatus may generate a disparity map regarding each of the left eye image and the right eye image using the left eye image and the right eye image that constitute a stereo image.

Part (a) of FIG. 4 is one of the left eye image and the right eye image that constitute the stereo image, and part (b) of FIG. 4 is a disparity map corresponding to the image illustrated in part (a) of FIG. 4.

Specifically, the disparity map may be expressed as a gray value corresponding to a distance. Referring to part (b) of FIG. 4, as the location difference between the corresponding points of the left eye image and the right eye image is great, the electronic apparatus expresses the disparity map with a bright gray value, and as the location difference of the corresponding points is small, the electronic apparatus expresses the disparity map with a dark gray value when generating the disparity map. Accordingly, the electronic apparatus may calculate the distance information between the object located at a specific location and a capturing point by using the gray value in a specific point in the disparity map.

Figure 5:
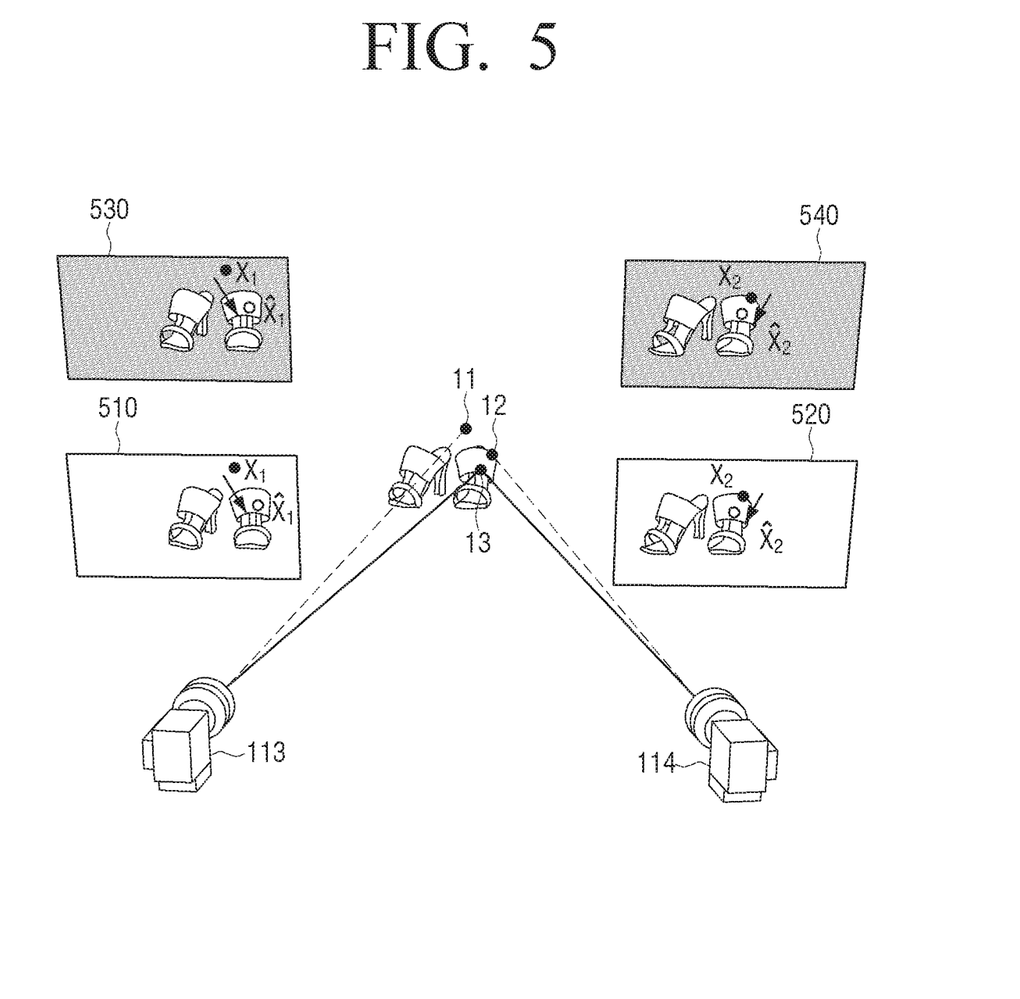
FIG. 5 is a view illustrating a method for compensating a watch point according to an embodiment.

FIG. 5 is a view illustrating a method for compensating a watch point according to an embodiment.

Referring to FIG. 5, the stereo cameras 113 and 114 may generate the stereo images 510 and 520 by capturing the direction corresponding to the gaze of a user. Specifically, the camera 113 corresponding to the left eye may generate the left eye image 510, and the camera 114 corresponding to the right eye may generate the right eye image 520. Here, the camera 113 corresponding to the left eye and the camera 114 corresponding to the right eye may be spaced apart from each other for a distance corresponding to the distance between the left eye and the right eye. In addition, the location difference of the corresponding point in the left eye image 510 and the right eye image 520 may corresponds to the distance between the left eye and the right eye.

The electronic apparatus may detect the left eye watch point ($X_1$) in the left eye image 510 and the right eye watch point ($X_2$) in the right eye image 520 using the binocular image. However, if the detected left eye watch point ($X_1$) and the detected right eye watch point ($X_2$) are matched and the watch point on the three-dimensional space is calculated, the left eye watch point 11 on the three-dimensional space and the right eye watch point 12 on the three-dimensional space may not correspond to each other, and accordingly, the electronic apparatus may not calculate an accurate watch point on the three-dimensional space.

According thereto, the electronic apparatus may generate the disparity map 530 regarding the left eye image 510 and the disparity map 540 regarding the right eye image 520. In addition, by using the generated disparity maps 530 and 540, the detected left eye watch point ($X_1$) and the detected right eye watch point ($X_2$) could be compensated respectively.

Specifically, the electronic apparatus may calculate the disparity of the detected left eye watch point ($X_1$) and the detected right eye watch point ($X_2$) respectively by using the disparity maps 530 and 540. Referring to FIG. 5, the disparity of the detected left eye watch point ($X_1$) is far and the disparity of the detected right eye watch point ($X_2$) is close, and thus the electronic apparatus may determine that the wrong watch point is detected.

In addition, the electronic apparatus may set the scope in which compensation could be performed respectively based on the detected left eye watch point ($X_1$) and the detected right eye watch point ($X_2$), and select the most appropriate left eye watch point ($\hat{X}_1$) and right eye watch point ($\hat{X}_2$) within the scope in which compensation could be performed. The operation for compensating a watch point has been described in the description regarding FIG. 1, and thus an overlapping description will be omitted.

In addition, the electronic apparatus may compensate the watch point with the selected left eye watch point ($\hat{X}_1$) and the selected right eye watch point ($\hat{X}_2$). In addition, the electronic apparatus may generate the watch point 13 on a three-dimensional space using the compensated left eye watch point ($\hat{X}_1$) and the compensated right eye watch point ($\hat{X}_2$). Referring to FIG. 5, the watch point on the three-dimensional space generated using the compensated left eye watch point ($\hat{X}_1$) is identical to the watch point on the three-dimensional space generated using the compensated right eye watch point ($\hat{X}_2$), and thus the electronic apparatus may generate the information on the generated watch point on the three-dimensional space. Here, the generated information may include the vector and distance information of a binocular gaze regarding the watch point on the three-dimensional space.

Figure 6:
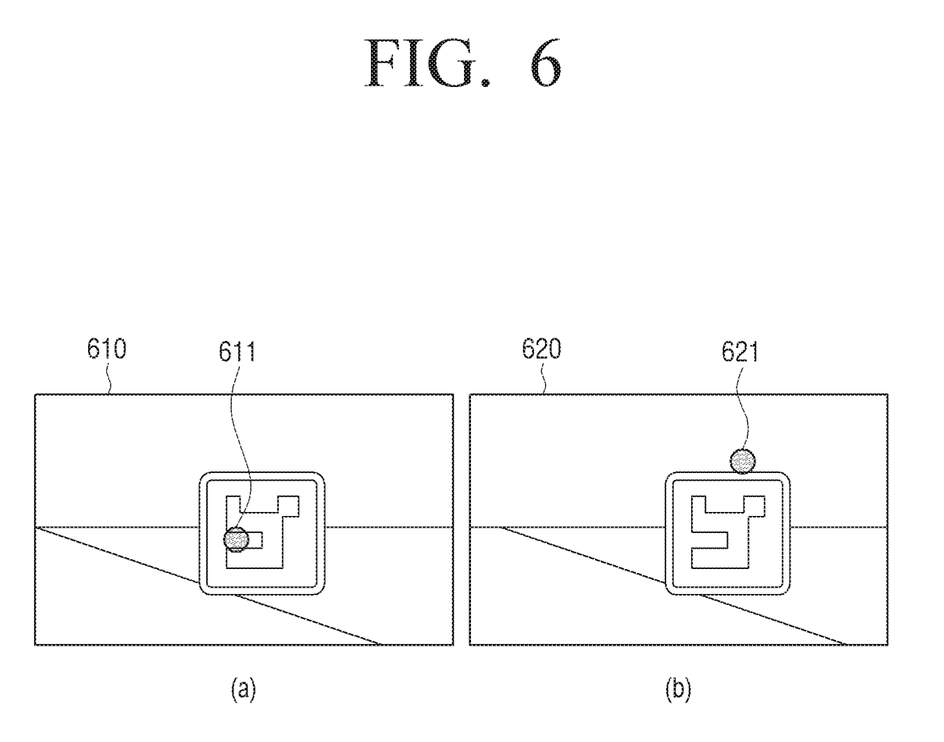
FIG. 6 is a view illustrating a watch point detected in a stereo image.
Figure 7:
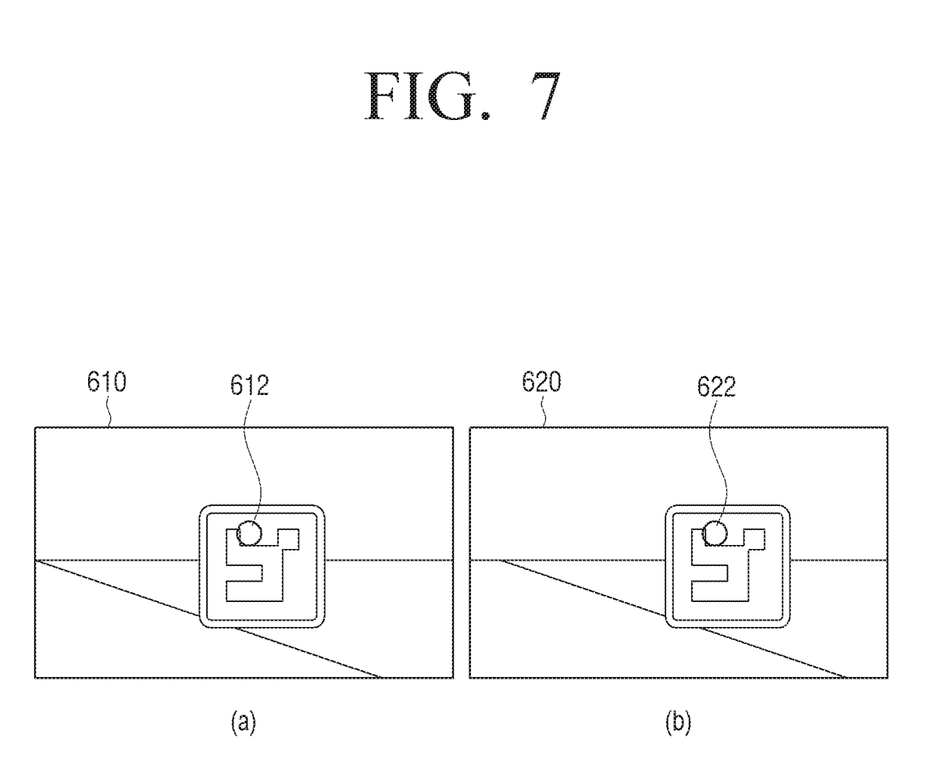
FIG. 7 is a view illustrating a watch point obtained by compensating a watch point of FIG. 6 according to an embodiment.

FIG. 6 is a view for describing a watch point detected in a stereo image. Specifically, part (a) of FIG. 6 is a left eye image 610, and part (b) of FIG. 6 is a right eye image 620. In addition, FIG. 7 is a view for illustrating a watch point generated by compensating the watch point of FIG. 6 according to an embodiment. Specifically, part (a) of FIG. 7 may be a left eye image 610 and part (b) of FIG. 7 is a right eye image 620.

Referring to FIG. 6, the left eye watch point 611 detected from the left eye image 610 is located on an object. On the contrary, the right eye watch point 621 detected from the right eye image 620 is located outside the object.

The electronic apparatus may generate a disparity map regarding each of the left eye image 610 and the right eye image 620, and determine that the disparity of the left eye watch point 611 does not correspond to the disparity of the right eye watch point 621 by using the generated disparity map. In addition, the electronic apparatus may compensate the left eye watch point 611 and the right eye watch point 621 using the disparity map.

Specifically, based on the left eye watch point 611 and the right eye watch point 621, the electronic apparatus may set the area in which a compensation may be performed respectively, and may select the most appropriate left eye watch point and right eye watch point so that a compensation distance is minimum in the area in which compensation may be performed and that the difference between the disparity of each compensated watch point is minimum.

The electronic apparatus may compensate the left eye watch point and the right eye watch point with the selected left eye watch point and the right eye watch point. As a result of performing the compensation according to an embodiment, as illustrated in FIG. 7, the compensated left eye watch point 613 in the left eye image 610 may be located on an object, and the compensated right eye watch point 622 in the right eye image 620 also may be located on an object.

As in the above, in a state in which the horizontal deviation of the left eye image 610 and the right eye image 620 is compensated, the electronic apparatus may perform compensation so that the location difference between the compensated left eye watch point 613 and the compensated right eye watch point 622 is minimized, and that the disparity difference between the compensated left eye watch point 613 and the compensated right eye watch point 622 is minimized.

Figure 8:
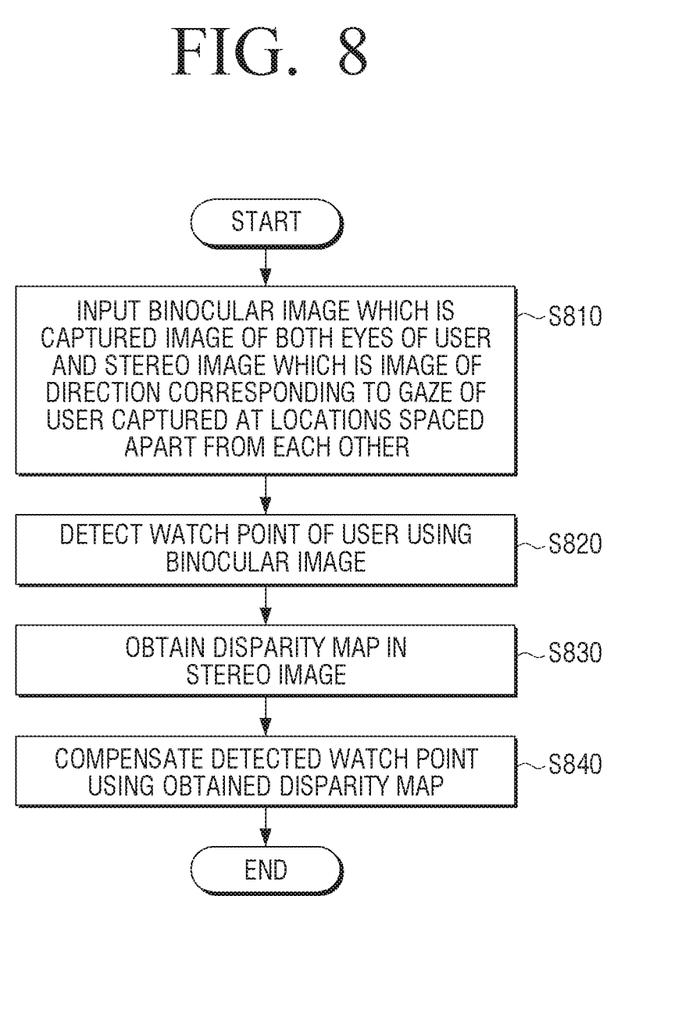
FIG. 8 is a flow chart illustrating a method for compensating a watch point according to an embodiment.

FIG. 8 is a flow chart illustrating a method for compensating a watch point according to an embodiment.

First, the electronic apparatus may receive a binocular image which is a captured image of both eyes of a user and a stereo image which is an image of a direction corresponding to a gaze of the user captured at locations spaced apart from each other, in S810. Specifically, the electronic apparatus may capture the binocular image and the stereo image using a plurality of included cameras. Meanwhile, if a camera is not included in the electronic apparatus, at least one of the binocular image and the stereo image may be received through an external apparatus.

Next, the electronic apparatus may detect the watch point of a user using the binocular image in S820. Specifically, the electronic apparatus may detect the watch point of the user in the stereo image using the binocular image.

In addition, the electronic apparatus may generate a disparity map in the input stereo image in S830. Specifically, the electronic apparatus may generate the disparity map regarding the left eye image and the right eye image respectively using the left eye image and the right eye image constituting the stereo image. Here, the electronic apparatus may generate a disparity map using the difference in the locations of a corresponding points in the left eye image and the right eye image.

Next, the electronic apparatus may compensate the detected watch point using the generated disparity map in S840. Specifically, the electronic apparatus may compensate the left eye watch point detected from the left eye image and the right eye watch point detected from the right eye image by using the disparity map generated regarding the left eye image and the disparity map generated regarding the right eye image. Here, the electronic apparatus may compensate the left eye watch point and the right eye watch point at one time.

As described above, according to compensating the left eye watch point and the right eye watch point using a disparity map, further accurate watch point of a user may be detected in a three-dimensional space.

Various embodiments described above may be implemented in a recording medium that may be read by a computer or a similar apparatus to the computer by using software, hardware, or a combination thereof. According to the hardware embodiment, exemplary embodiments that are described in the present disclosure may be implemented by using at least one selected from Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, electrical units for performing other functions. In some cases, exemplary embodiments that are described in the present disclosure may be embodied as the processor 120 itself. In a software embodiment, various embodiments described in the present disclosure such as a procedure and a function may be implemented as separate software modules. The software modules may respectively perform one or more functions and operations described in the exemplary embodiments.

Methods of controlling an electronic apparatus according to various exemplary embodiments may be stored in a non-transitory readable medium. The non-transitory readable medium may be installed and used in various devices.

The non-transitory computer readable medium is not a medium that stores data for a short moment such as a register, a cache and a memory and the like, but a medium that stores data semi-permanently and which is readable by an apparatus. Specifically, programs for performing the above-described various methods can be stored in a non-transitory computer readable medium such as a CD, a DVD, a hard disk, a Blu-ray disk, universal serial bus (USB), a memory card, ROM, or the like, and can be provided.

Although various example embodiments of the present disclosure have been illustrated and described hereinabove, the present disclosure is not limited to the above-mentioned example embodiments, but may be variously modified by those skilled in the art to which the present disclosure pertains without departing from the scope and spirit of the disclosure as set forth in the accompanying claims. These modifications should also be understood to fall within the scope of the present disclosure.

What is claimed is:

1. An electronic apparatus comprising:
a camera configured to receive a binocular image which is a captured image of both eyes of a user and a stereo image which comprises two images of a direction corresponding to a gaze of the user captured at locations spaced apart from each other, the stereo image including a first image corresponding to a left eye of the user and a second image corresponding to a right eye of the user; and
a processor configured to:
detect a left watch point of a user in the first image and a right eye watch point of the user in the second image by using the binocular image,
obtain a first disparity map and a second disparity map by performing stereo matching of the first image and the second image, and
compensate the detected eye watch point and the detected right eye watch point by using the first disparity map and the second disparity map.

2. The electronic apparatus as claimed in claim 1, wherein the processor is further configured to compensate the detected left eye watch point and the detected right eye watch point using the first disparity map and the second disparity map to minimize a difference between a disparity of the left eye watch point and a disparity of the right eye watch point.

3. The electronic apparatus as claimed in claim 1, wherein the processor is further configured to compensate the detected left eye watch point and the detected right eye watch point to minimize a difference between a location of the left eye watch point and a location of the right eye watch point in a state in which horizontal deviation of the first image and the second image is compensated.

4. The electronic apparatus as claimed in claim 3, wherein the processor is further configured to obtain a three-dimensional watch point using the compensated left eye watch point and the compensated right eye watch point.

5. The electronic apparatus as claimed in claim 3, wherein the processor is further configured to obtain vector and distance information of a binocular gaze using the compensated left eye watch point and the compensated right eye watch point.

6. The electronic apparatus as claimed in claim 1, wherein the processor is further configured to:
compensate vertical deviation of the first image and the second image, and
perform stereo matching using the compensated first image and the compensated second image.

7. The electronic apparatus as claimed in claim 1, wherein the camera comprises:
an infrared camera configured to captures both eyes of the user; and
a stereo camera configured to capture a direction corresponding to a gaze of the user at locations spaced apart from each other.

8. A method for controlling an electronic apparatus comprising:
receiving a binocular image which is a captured image of both eyes of a user and a stereo image which comprises two images of a direction corresponding to a gaze of the user captured at locations spaced apart from each other, the stereo image including a first image corresponding to a left eye of the user and a second image corresponding to a right eye of the user;
detecting a left eye watch point of a user in the first image and a right eye watch point in the second image by using the binocular image;
obtaining a first disparity map and a second disparity map by performing stereo matching of the first image and the second image; and
compensating the detected left eye watch point and the detected right eye watch point by using the first disparity map and the second disparity map.

9. The controlling method as claimed in claim 8, wherein the compensating comprises compensating the detected left eye watch point and the detected right eye watch point using the first disparity map and the second disparity map to minimize a difference between a disparity of the left eye watch point and a disparity of the right eye watch point.

10. The controlling method as claimed in claim 8, wherein the compensating comprises compensating the detected left eye watch point and the detected right eye watch point to minimize a difference between a location of the left eye watch point and a location of the right eye watch point in a state in which horizontal deviation of the first image and the second image is compensated.

11. The controlling method as claimed in claim 10, further comprising:
obtaining a three dimensional watch point using the compensated left eye watch point and the compensated right eye watch point.

12. The controlling method as claimed in claim 10, further comprising:
obtaining vector and distance information of a binocular gaze using the compensated left eye watch point and the compensated right eye watch point.

13. The controlling method as claimed in claim 8, further comprising:
compensating vertical deviation of the first image and the second image;
wherein the obtaining comprises performing stereo matching using the compensated first image and the compensated second image.

14. The controlling method as claimed in claim 8, wherein the receiving comprises capturing both eyes of the user using an infrared camera, and capturing a direction corresponding to a gaze of the user at locations spaced apart from each other.

15. A non-transitory computer readable recording medium which includes a program to execute a method for controlling an electronic apparatus,
wherein the controlling method comprises:
receiving a binocular image which is a captured image of both eyes of a user and a stereo image which comprises two images of a direction corresponding to a gaze of the user captured at locations spaced apart from each other, the stereo image including a first image corresponding to a left eye of the user and a second image corresponding to a right eye of the user;
detecting a left eye watch point of a user in the first image and a right eye watch point in the second image by using the binocular image;
obtaining a first disparity map and a second disparity map by performing stereo matching of the first image and the second image; and
compensating the detected left eye watch point and the detected right eye watch point by using the first disparity map and the second disparity map.

* * * * *